(12) United States Patent
Chinnock et al.

(10) Patent No.: US 11,633,091 B2
(45) Date of Patent: Apr. 25, 2023

(54) METHOD AND APPARATUS FOR ILLUMINATING AN OBJECT FIELD IMAGED BY AN IMAGE SENSOR

(71) Applicant: Titan Medical Inc., Toronto (CA)

(72) Inventors: Randal B. Chinnock, Ashford, CT (US); William L. Weber, Olivebridge, NY (US)

(73) Assignee: Titan Medical Inc., Toronto (CA)

( * ) Notice: Subject to any disclaimer, the term of this patent is extended or adjusted under 35 U.S.C. 154(b) by 110 days.

(21) Appl. No.: 17/366,483

(22) Filed: Jul. 2, 2021

(65) Prior Publication Data

US 2021/0401278 A1 Dec. 30, 2021

Related U.S. Application Data

(63) Continuation of application No. 17/028,025, filed on Sep. 22, 2020, now Pat. No. 11,051,686, which is a
(Continued)

(51) Int. Cl.
*A61B 1/07* (2006.01)
*G03B 11/00* (2021.01)
(Continued)

(52) U.S. Cl.
CPC .............. *A61B 1/07* (2013.01); *A61B 1/0017* (2013.01); *A61B 1/00096* (2013.01);
(Continued)

(58) Field of Classification Search
CPC ..... A61B 1/07; A61B 1/00096; A61B 1/0017; A61B 1/00186; A61B 1/00188;
(Continued)

(56) References Cited

U.S. PATENT DOCUMENTS 3,812,374 A 5/1974 Tuhro
5,838,865 A 11/1998 Gulick
(Continued)

FOREIGN PATENT DOCUMENTS

EP 1 570 863 A1 9/2005
JP 2009246770 A 10/2009
WO WO 2003/021329 A2 3/2003

OTHER PUBLICATIONS

European Examination Report in European Application No. 16 838 146.5, dated Apr. 30, 2020 in 5 pages.
(Continued)

*Primary Examiner* — Bryon T Gyllstrom
(74) *Attorney, Agent, or Firm* — Knobbe, Martens, Olson & Bear, LLP

(57) ABSTRACT

An illuminator apparatus and method for illuminating an object field imaged by a rectangular image sensor having a first aspect ratio is disclosed. The apparatus includes an optical fiber having a proximal end disposed to receive a plurality of input light beams, each light beam having differing spectral properties, the optical fiber being operable to transmit the light beams along the fiber to a distal end of the optical fiber. The apparatus also includes an integrating element disposed to receive the light beams from the distal end of the fiber and combine the light beams to produce a generally homogenous illumination beam at a rectangular output face of the integrating element. The apparatus further includes an illumination projector operable to project an image of the output face of the integrating element into the object field to produce a generally rectangular illuminated region of the object field substantially corresponding to the portion of the object field imaged by the rectangular image sensor.

16 Claims, 3 Drawing Sheets

Related U.S. Application Data continuation of application No. 16/512,682, filed on Jul. 16, 2019, now Pat. No. 10,820,791, which is a continuation of application No. 15/754,566, filed as application No. PCT/CA2016/000215 on Aug. 23, 2016, now Pat. No. 10,357,147.

(60) Provisional application No. 62/209,157, filed on Aug. 24, 2015.

(51) Int. Cl.

| | | |
|---|---|---|
| *G03B 15/02* | (2021.01) | |
| *G03B 15/14* | (2021.01) | |
| *H04N 5/225* | (2006.01) | |
| *A61B 1/00* | (2006.01) | |
| *A61B 1/045* | (2006.01) | |
| *A61B 1/05* | (2006.01) | |
| *A61B 1/06* | (2006.01) | |
| *A61B 1/313* | (2006.01) | |

(52) U.S. Cl.
CPC ...... *A61B 1/00186* (2013.01); *A61B 1/00188* (2013.01); *A61B 1/045* (2013.01); *A61B 1/051* (2013.01); *A61B 1/0638* (2013.01); *A61B 1/0669* (2013.01); *A61B 1/3132* (2013.01); *G03B 11/00* (2013.01); *G03B 15/02* (2013.01); *G03B 15/14* (2013.01); *H04N 5/2251* (2013.01); *H04N 5/2256* (2013.01)

(58) Field of Classification Search
CPC ....... A61B 1/045; A61B 1/051; A61B 1/0638; A61B 1/0669; A61B 1/3132; G03B 15/02; G03B 15/14; H04N 5/2251; H04N 5/2256

See application file for complete search history.

(56) References Cited

U.S. PATENT DOCUMENTS

| | | |
|---|---|---|
| 7,245,280 B2 | 7/2007 | Park |
| 8,169,466 B2 | 5/2012 | Iketani et al. |
| 8,872,906 B2 | 10/2014 | Bayer et al. |
| 10,357,147 B2 | 7/2019 | Chinnock et al. |
| 10,820,791 B2 | 11/2020 | Chinnock et al. |
| 2001/0056282 A1* | 12/2001 | Sonnenschein .... A61B 17/0686 606/139 |
| 2008/0310181 A1* | 12/2008 | Gurevich ............ G02B 6/0008 362/554 |
| 2010/0110389 A1* | 5/2010 | Liao .................... G03B 21/14 353/31 |
| 2010/0231862 A1* | 9/2010 | Itoh ..................... H04N 9/3161 353/38 |
| 2011/0082452 A1 | 4/2011 | Melsky et al. |
| 2011/0234782 A1* | 9/2011 | Ehrhardt ............. A61B 1/0684 362/574 |
| 2012/0242959 A1 | 9/2012 | Huang |
| 2014/0005483 A1* | 1/2014 | Ohashi ................ A61B 1/0684 600/162 |
| 2014/0362200 A1* | 12/2014 | Kanamori ........ A61B 1/000095 348/70 |
| 2018/0146839 A1* | 5/2018 | Friedlander ........ A61B 1/00042 |
| 2018/0276843 A1* | 9/2018 | Send ........................ G01C 3/08 |
| 2019/0087968 A1* | 3/2019 | Grunnet-Jepsen ...... G06T 7/521 |
| 2021/0000335 A1 | 1/2021 | Chinnock et al. |

OTHER PUBLICATIONS

Extended European Search Report in EP Application No. 16838146.5, dated May 16, 2018.
Fan, F. et al., "A Monolithic White Laser;" Nature in Nanotechnology, Jul. 2015, pp. 1-16.
International Search Report and Written Opinion received in PCT Application No. PCT/CA2016/000215, dated Nov. 15, 2016 in 7 pages.
Notice of Allowance received in Canadian Patent Application No. 2,996,014, dated Jun. 4, 2018.

* cited by examiner

METHOD AND APPARATUS FOR ILLUMINATING AN OBJECT FIELD IMAGED BY AN IMAGE SENSOR

CROSS-REFERENCE TO RELATED APPLICATIONS

This application is a continuation of U.S. patent application Ser. No. 17/028,025, filed on Sep. 22, 2020 and issued as U.S. Pat. No. 11,051,686 on Jul. 6, 2021, which is a continuation of U.S. patent application Ser. No. 16/512,682, filed on Jul. 16, 2019 and issued as U.S. Pat. No. 10,820,791 on Nov. 3, 2020, which is a continuation of U.S. patent application Ser. No. 15/754,566, filed on Feb. 22, 2018 and issued as U.S. Pat. No. 10,357,147 on Jul. 23, 2019, which is a U.S. National Phase Application under 35 U.S.C. 371 of International Application No. PCT/CA2016/000215, filed on Aug. 23, 2016 and published as WO 2017/031568 A1 on Mar. 2, 2017, which claims priority to U.S. Provisional Application No. 62/209,157, filed on Aug. 24, 2015. The entire disclosures of all of the above applications are incorporated herein by reference.

BACKGROUND

1. Field

This disclosure relates generally to imaging and more particularly to illuminating an object field imaged by a rectangular image sensor.

2. Description of Related Art

Imaging using CMOS or CCD image sensors relies on the object field being illuminated to enable the imaging system to capture sufficient light for the image sensor to generate an image signal. If insufficient light is captured by the imaging system, the generated image signal may be too noisy to produce a useable image representation. When imaging in enclosed spaces there is usually a lack of ambient light and object field illumination must be provided. In some applications, such as imaging for laparoscopic surgery, there are limitations on the amount of heat that can be generated within the enclosed space. Accordingly there remains a need for improved illumination methods and apparatus for such applications.

SUMMARY

In accordance with one disclosed aspect there is provided an illuminator apparatus for illuminating an object field imaged by a rectangular image sensor having a first aspect ratio. The apparatus includes an optical fiber having a proximal end disposed to receive a plurality of input light beams, each light beam having differing spectral properties, the optical fiber being operable to transmit the light beams along the fiber to a distal end of the optical fiber. The apparatus also includes an integrating element disposed to receive the light beams from the distal end of the fiber and combine the light beams to produce a generally homogenous illumination beam at a rectangular output face of the integrating element. The apparatus further includes an illumination projector operable to project an image of the output face of the integrating element into the object field to produce a generally rectangular illuminated region of the object field substantially corresponding to the portion of the object field imaged by the rectangular image sensor.

The illuminated region of the object field may have a second aspect ratio and the first aspect ratio and the second aspect ratio may be substantially equivalent.

The illuminated region may be sized to cause the rectangular image sensor to be at least partly overfilled in at least one direction.

The apparatus may include a plurality of light sources, each light source being operable to generate one of the plurality of light beams.

The plurality of light sources may include two or more of a red laser source, a green laser source, a blue laser source, and a tunable laser source.

The apparatus may include a controller operably configured to sequentially activate each light source to cause the object field to be sequentially illuminated by each light beam, synchronize the image sensor to capture separate image frames while the object field is being illuminated by each light beam, and combine the captured image frames to produce a combined image of the object field.

The image sensor may include a plurality of sensor elements each element being responsive to light having spectral properties associated encompassing the spectral properties of the plurality of light beams and the separate image frames may be captured using all sensor elements in the plurality of sensor elements.

The apparatus may include a controller operably configured to control respective power levels of each of the plurality of light sources to produce a desired spectral illumination characteristic for the illuminated region.

The desired spectral characteristic may be selected to enhance certain features within the object field.

The image sensor may have reduced sensitivity to some spectral components and the desired spectral characteristic may be selected to increase a power level associated with spectral components having reduced sensitivity.

The illumination projector may include a first polarizer to cause the illuminated region to be illuminated by polarized light having a first polarization direction and images captured by the image sensor may be captured through a second polarizer having a second polarization direction operable to reduce specular reflections from objects within the object field.

In accordance with another disclosed aspect there is provided a method for illuminating an object field imaged by a rectangular image sensor having a first aspect ratio. The method involves receiving a plurality of input light beams having differing spectral properties at a proximal end of an optical fiber, transmitting the light beams along the fiber to a distal end of the fiber, and coupling the light beams from the distal end of the fiber into an integrating element operable to combine the light beams to produce a generally homogeneous illumination beam at a rectangular output face of the integrating element. The method also involves projecting an image of the output face of the integrating element into the object field to produce a generally rectangular illuminated region of the object field substantially corresponding to the portion of the object field imaged by the rectangular image sensor.

Producing the generally rectangular illuminated region may involve producing a generally rectangular illuminated region having a second aspect ratio and the first aspect ratio and the second aspect ratio may be substantially equivalent.

Producing the generally rectangular illuminated region may involve producing a generally rectangular illuminated region sized to cause the rectangular image sensor to be at least partly overfilled in at least one direction.

Receiving the plurality of light beams may involve activating each of a plurality of light sources, each light source being operable to produce one of the plurality of light beams.

Activating may involve activating two or more of a red laser source, a green laser source, a blue laser source, and a tunable laser source, to produce respective light beams in the plurality of light beams.

The method may involve sequentially activating each light source to cause the object field to be sequentially illuminated by each light beam, synchronizing the image sensor to capture separate image frames while the object field is being illuminated by each light beam, and combining the captured image frames to produce a combined image of the object field.

The image sensor may involve a plurality of sensor elements each element being responsive to light having spectral properties encompassing each of the plurality of light beams and the separate image frames may be captured using all sensor elements in the plurality of sensor elements.

Actuating each of a plurality of light sources to produce one of the plurality of light beams may involve controlling respective power levels of each of the plurality of light sources to produce a desired spectral illumination characteristic for the illuminated region.

The desired spectral characteristic may be selected to enhance certain features within the object field.

The image sensor has reduced sensitivity to some spectral components and the desired spectral characteristic may be selected to increase a power level associated with spectral components having reduced sensitivity.

Projecting the image of the output face of the integrating element may involve projecting the image through a first polarizer such that the object field may be illuminated by polarized light having a first polarization direction and images captured by the image sensor may be captured through a second polarizer having a second polarization direction operable to reduce specular reflections from objects within the object field.

Other aspects and features will become apparent to those ordinarily skilled in the art upon review of the following description of specific disclosed embodiments in conjunction with the accompanying figures.

BRIEF DESCRIPTION OF THE DRAWINGS

In drawings which illustrate disclosed embodiments.

DETAILED DESCRIPTION

Figure 1:
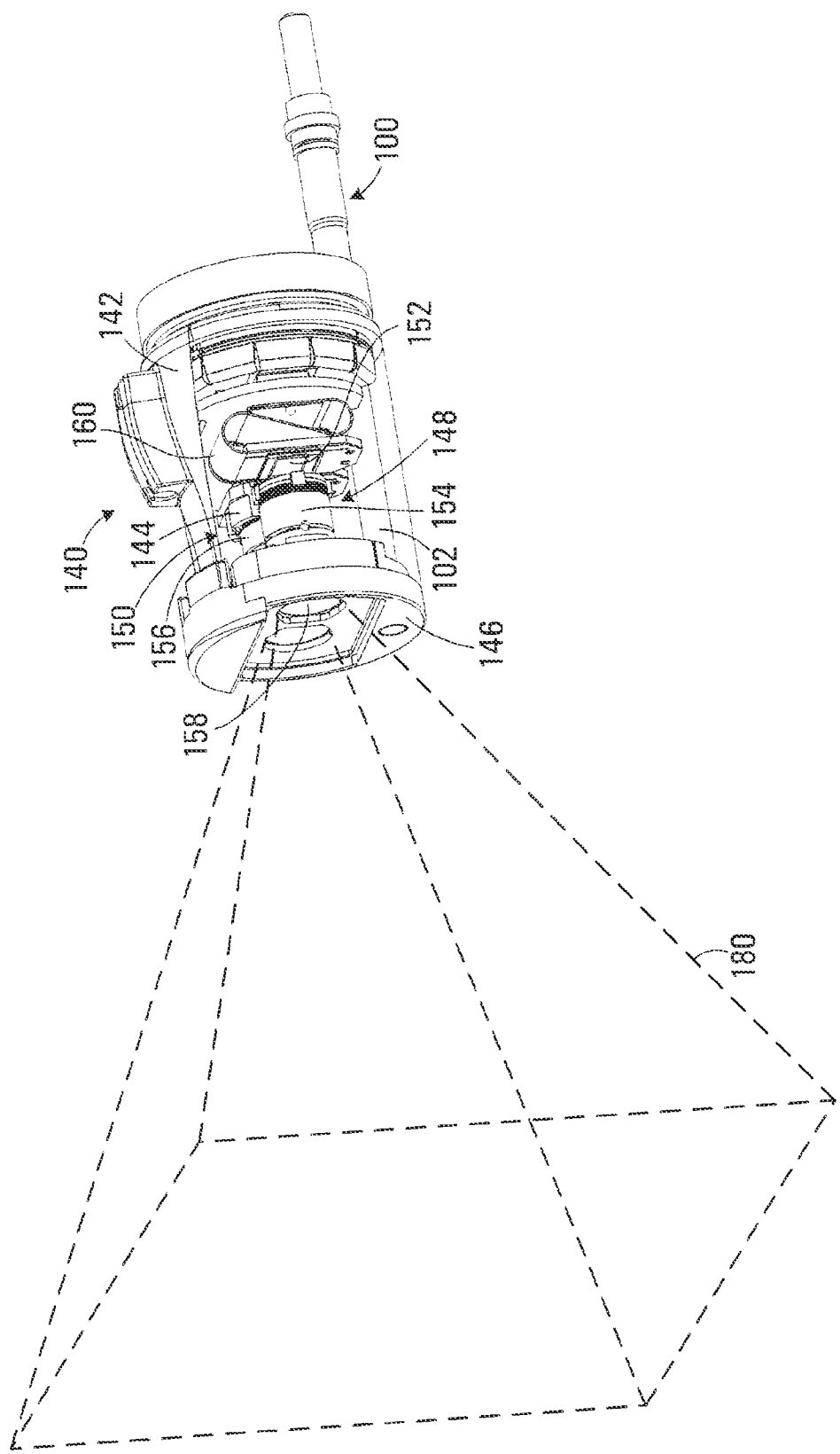
FIG. 1 is a perspective view of an illuminator apparatus in conjunction with a camera according to a first disclosed embodiment.

Referring to FIG. 1, an illuminator apparatus according to a first disclosed embodiment is shown generally at 100. The illuminator apparatus 100 is shown in conjunction with a camera 140. The illuminator apparatus 100 and camera 140 are located within an enclosure 142, which is shown partially cut away in FIG. 1. The illuminator apparatus 100 includes a housing 102 that extends through the enclosure 142 and terminates at a front face 146 of the camera 140.

In this embodiment the camera 140 includes a first imager 148 and second imager 150, which are spaced apart and configured to generate stereoscopic views of 3 dimensional objects located within an object field 180. The first and second imagers 148 and 150 are symmetrically configured. The first imager 148 includes an image sensor 152 and a lens assembly 154. The second imager 150 also includes an image sensor and a lens assembly 156. In FIG. 1 the image sensor of the second imager 150 is obscured by a mounting bezel 144, which holds and aligns the lens assembly 156 with respect to the image sensor. The first imager 148 has a corresponding mounting bezel, which has been removed in FIG. 1 to reveal the image sensor 152. The lens assemblies 154 and 156 each house a plurality of optical elements (not shown) for capturing light from the object field 180 and producing images of the object at the respective image sensors of the imagers 148 and 150.

The image sensors may be CMOS active pixel image sensors or a charge coupled device (CCD) image sensors having a plurality of picture elements (pixels) disposed in a rectangular matrix. The pixels make up an active area of the image sensors and the ratio of the width to height of the active area defines an aspect ratio for the image sensor. In one embodiment the image sensors may each be implemented using a 0.2 inch 1920×1080 pixel image sensor having a 16:9 aspect ratio and may also include spectral band filters for each individual pixel, such as RGB filters arranged in a Bayer pattern.

The first imager 148 receives light from the object field 180 through an input end 158 of the lens assembly 154 and images the light onto the image sensor 152 to capture an image of the object field from a first perspective viewpoint. The image sensor 152 generates first data signals representing the light energy received at each pixel, which are coupled through an electrical connector 160 to an output of the camera 140. Similarly, the lens assembly 156 of the second imager 150 captures an image of the object field from a second perspective viewpoint and the corresponding image sensor (not shown in FIG. 1) generates second data signals representing the image. The data signals from the imagers 148 and 150 are transmitted back to an image processor (not shown) where they are combined and displayed to provide a composite image that conveys three-dimensional (3D) spatial information to the viewer.

In other embodiments, the camera 140 may be implemented as a conventional camera having a single imager and lens assembly for producing two-dimensional (2D) image views.

Figure 2:
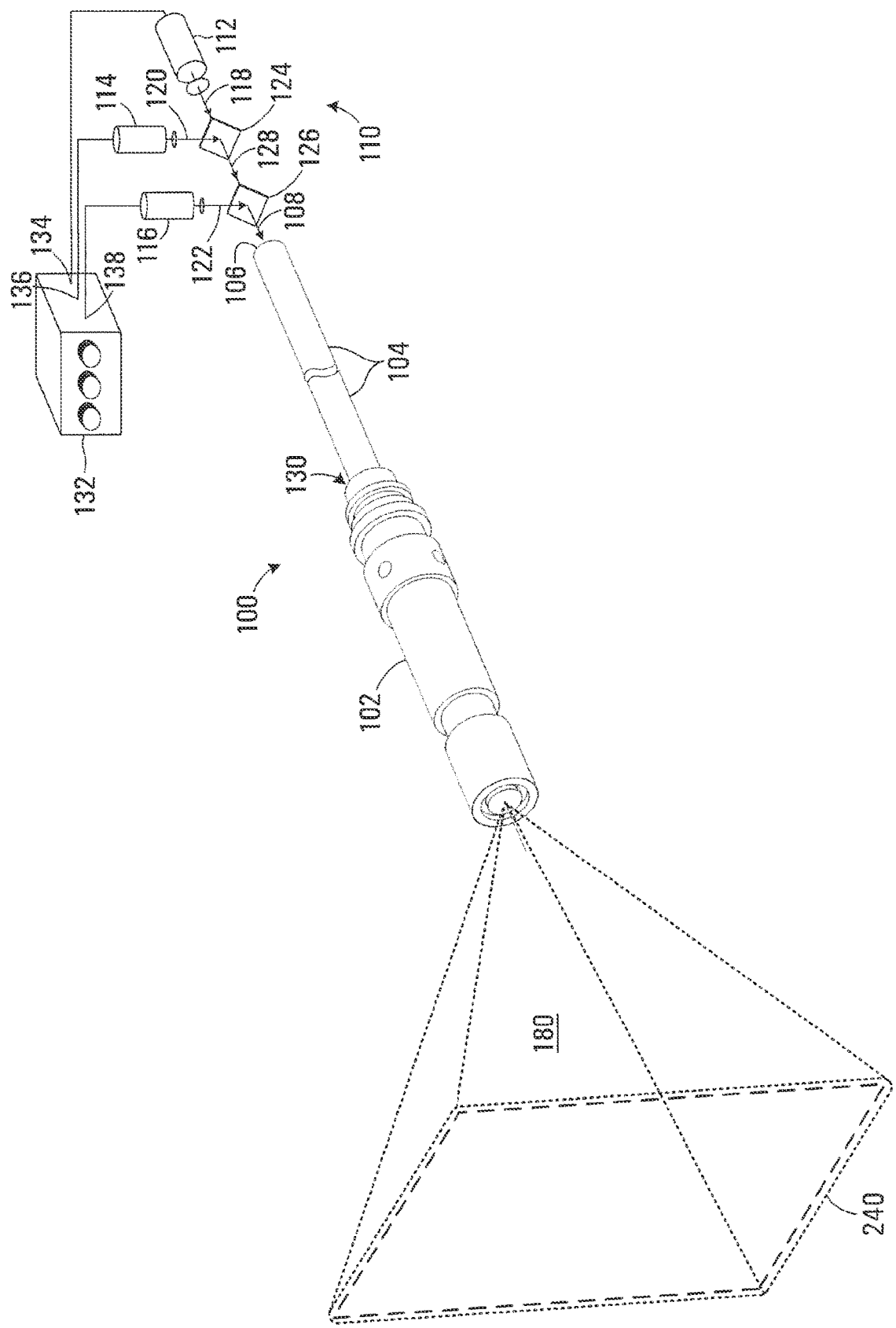
FIG. 2 is a further perspective view of the illuminator apparatus shown in FIG. 1.

The illuminator apparatus 100 is shown in FIG. 2 in combination with a light generator 110. Referring to FIG. 2, the illuminator apparatus 100 includes an optical fiber 104 having a proximal end 106, which is disposed to receive a composite light beam 108 from the light generator 110. The composite light beam 108 includes a plurality of input light beams each having differing spectral properties. In one embodiment the plurality of light beams each has a limited wavelength range and a differing center wavelength.

In the embodiment shown the light generator 110 includes a plurality of light sources 112, 114, and 116, each of which generates a respective light beam 118, 120, and 122. The light generator 110 further includes first and second beam combining mirrors 124 and 126. The first mirror 124 is configured to transmit the light beam 118 from the light source 112 through the mirror while reflecting the beam 120 from the light source 114 to produce a light beam 128.

Similarly, the second mirror 126 is configured to transmit the light beam 128 through the mirror while reflecting the beam 122 from the light source 116 to produce the composite light beam 108. In one embodiment the first and second mirrors may include dichroic coatings for configuring the transmission and reflectance properties. The composite light beam 108 thus includes spectral contributions from each of the sources 112, 114, and 116. In one embodiment the sources 112, 114, and 116 are each implemented using a laser source such as a laser diode. In one embodiment the sources 112, 114, and 116 are respectively red, green, and blue laser diodes (RGB lasers) and the composite light beam 108 has a combined spectral content generally approximating white light. The composite light beam 108 thus includes three separate substantially coaxial beams 118, 120, and 122.

While the embodiment shown in FIG. 2 combines beams from three sources to produce the composite light beam 108, more than three sources may be combined to provide a desired spectrum of the composite light beam. In one embodiment one or more of the sources may also be selectively activated to provide specific wavelength content in the composite light beam 108. For example, in imaging situations where a specific wavelength of illumination facilitates discernment of certain features having a unique spectral reflectance, the wavelength may be provide by selectively activating a source that produces light including the specific wavelength. Alternatively or additionally, the sources may include one or more tunable laser sources to facilitate a wide selection of specialized wavelengths, which may also be used in combination or in sequence with fixed wavelength sources such as RGB lasers.

The optical fiber 104 is operable to transmit the composite light beam 108 along the fiber to a distal end 130 of the optical fiber located within the housing 102. In one embodiment the optical fiber 104 is sufficiently long to permit the housing 102 of the illuminator apparatus 100 to be located within an enclosed space while the light generator 110 is located outside the enclosed space. In this embodiment, heat generated by operation of the light generator 110 is thus not directly conducted into the enclosed space.

Figure 3:
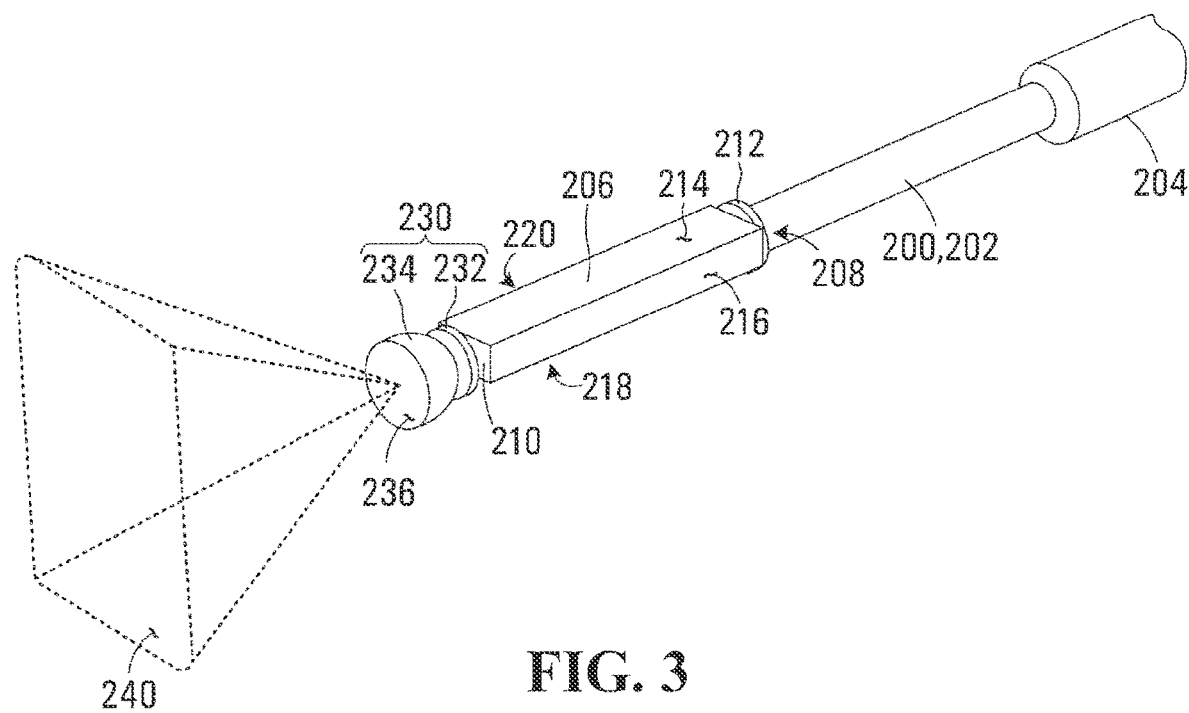
FIG. 3 is a perspective view of optical components of the illuminator apparatus shown in FIG. 1 and FIG. 2.

The illuminator apparatus 100 is shown in FIG. 3 with the housing 102 removed to reveal optical components within. The layout of the optical components is further shown in plan view in FIG. 4. Referring to FIG. 3, the optical fiber 104 includes a core 200, a cladding 202, and a jacket 204. The refractive indices of the core 200 and the cladding 202 are selected to cause the composite light beam 108 received at the proximal end 106 to be substantially confined within the core, internally reflecting all rays within a design numerical aperture (NA) of the fiber. The jacket 204 is stripped away within the housing 102 to expose a portion of the core 200 and the cladding 202 and the stripped end is cleaved at a distal end 300. The core 200 may comprise polymethyl methacrylate (PMMA) and may have a diameter of about 720 µm for use with the RGB laser sources described above.

The illuminator apparatus 100 further includes an integrating element 206 having an input face 208 and an output face 210. In the embodiment shown, the light beams are coupled from the distal end 300 of the optical fiber 104 via a lens 212 into the input face 208 of the integrating element 206. In this embodiment the lens 212 has a plano-concave shape and an index-matching gel or optical cement may be introduced between the fiber and the lens and/or the lens and the input face to enhance coupling of the composite light beam 108 into the integrating element 206. In other embodiments the lens 212 may be omitted and the light beams may be coupled directly from the distal end 300 of the optical fiber 104 into the integrating element 206.

Figure 4:
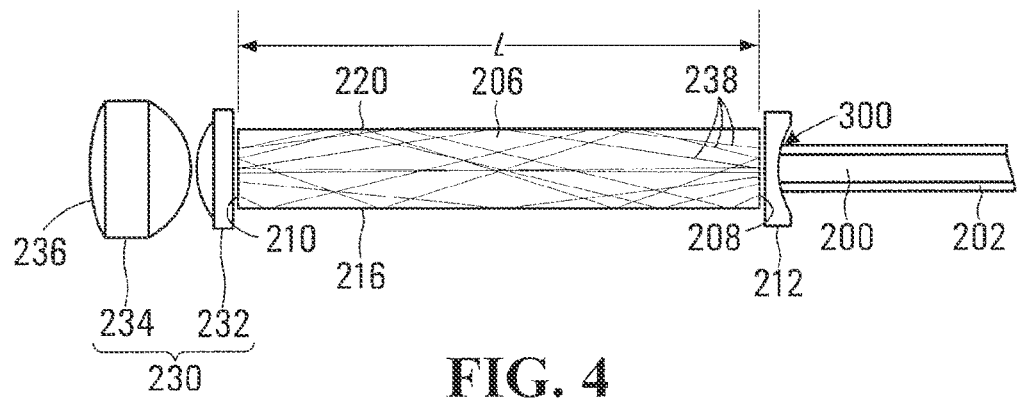
FIG. 4 is a plan view of the optical components of the illuminator apparatus shown in FIG. 3.

The integrating element 206 mixes and combines the individual light beams making up the composite light beam 108 to produce a uniform generally homogenous illuminated area at the output face 210. The illuminated area at the output face 210 has generally uniform radiance. In the embodiment shown the integrating element 206 is implemented using a rectangular optical element having polished planar outer surfaces 214, 216, 218, and 220, rectangular input and output faces 208 and 210. Substantially all rays in the composite light beam 108 coupled into the integrating element 206 from the optical fiber 104 undergo a plurality of total internal reflections within the element causing the constituent beams 118, 120, and 122 from the sources 112, 114, and 116 to be mixed and combined into light beam with generally homogenous irradiance at the output face 210. A plurality of representative light rays 238 are shown in FIG. 4 undergoing internal reflections at the surfaces 216 and 220. Similar internal reflections occur at the surfaces 214 and 218. The spectral and spatial content in the beams 118, 120, and 122 is thus mixed by the integrating element 206, which also has the effect of reducing laser speckle due to rays having differing angles at the output face 210. In contrast the composite light beam 108 may include some regions that have differing spectral or spatial content to other regions due to misalignment and other effects and further may exhibit more pronounced laser speckle. The degree of mixing of the beams 238 within the integrating element 206 is dependent in part on the length L of the element, with a longer element generally providing more homogenous illumination at the output face 210. In one embodiment where the sources 112, 114 and 116 are implemented using RGB lasers the length L of the integrating element 206 may be about 10 mm and the input face 208 and output face 210 may each have rectangular dimensions of about 1.5 mm by about 1.0 mm with an index of refraction near 1.52. Other embodiments may have differing dimensions depending on the application and illumination sources used.

In an alternative embodiment, a tapered rectangular integrating element having a gradually changing width and/or aspect along its length may be used to transform the numerical aperture (NA) and the area of the mixed and homogenized beams. In this embodiment, the side faces of the integrating element need not be planar. In yet another embodiment, the integrator may be implemented as a "fly's eye" integrator, which employs lenslet arrays to yield a uniform distribution of light.

The illuminator apparatus 100 also includes an illumination projector 230 that is operable to project an image of the output face 210 of the integrating element 206 into the object field 180 to produce a generally rectangular illuminated region 240. Since the light at the output face 210 is generally uniform the illumination of the region 240 will also be generally uniform. In this embodiment the illumination projector 230 includes a plano-convex lens 232 and a biconvex lens 234. A portion of front surface 236 of the biconvex lens 234 or its outer diameter may be sealed to the housing 102 to provide an optical interface between the illuminator apparatus 100 and the object field. In one embodiment, the plano-convex lens 232 may be optically coupled to the output face 210 of the integrating element 206 using an index matching gel or optical cement. In another embodiment the plano-convex lens 232 may be spaced away from the output face 210 of the integrating element 206. In some embodiments the plano surface of lens 232 may be replaced with a non-plano surface.

Referring back to FIG. 2, the illuminated region 240 produced by the illuminator apparatus 100 substantially corresponds to the object field 180 that is imaged by the first and second imagers 148 and 150 of the camera 140 onto the respective image sensors. In the embodiment shown the illuminated region 240 is slightly larger than the object field 180, while having an aspect ratio that is substantially equivalent to the aspect ratio of the image sensors of the first and second imagers 148 and 150. The slightly larger illuminated region 240 compensates for any reduction in illumination intensity proximate the edges of the illuminated region and the illuminated area thus overfills the respective image sensors when the object field is imaged onto the image sensors. The larger illuminated region 240 may also be useful in accounting for manufacturing and alignment variations, or parallax between the illumination and axes of the first and second imagers 148 and 150.

In one embodiment where the light sources 112, 114, and 116 comprise RGB lasers, the image sensors may be implemented using a full color image sensor that has different pluralities of pixels responsive to the different wavelength ranges produced by the sources. Full color image sensors usually include a color filter array such as a Bayer filter that has filter elements aligned with each pixel that cause the underlying pixel to be responsive only to a reduced range of wavelengths, such as red, green or blue wavelength bands. A Bayer filter uses cells of 4 pixels i.e. a red pixel, a blue pixel, and two green pixels to represent RGB color. Illumination of the object field 180 with light having red, green and blue wavelengths produces corresponding reflections that are captured by the camera 140 and impinge on the color filter of the image sensor. Pixels of the image sensor that underlie red filter elements produce an output signal in response to red light, while the green and blue responsive pixels produce signals in response to the respective green and blue spectral components of the reflected light. A single image sensor thus has a spatial resolution per color that is less than the overall spatial resolution of the image sensor. This reduction may potentially be avoided by using, a video prism, for example, to split each of the colors to a separate image sensors for red, green and blue spectral components, however the resulting size of the camera may be unacceptable for use in enclosed space applications such as laparoscopic surgery.

In an alternative embodiment, the illuminator apparatus 100 may be configured to illuminate the object field 180 sequentially in time using red, green, and blue light. Referring back to FIG. 2, in the embodiment shown the illuminator apparatus 100 includes a controller 132 having outputs 134, 136, and 138 for controlling the respective sources 112, 114, and 116. In one embodiment, the controller 132 is configured to sequentially activate each light source 112, 114, and 116 to cause the object field 180 to be sequentially illuminated by each wavelength band at different times. The camera 140 may be configured to synchronize the image sensor 152 to capture separate image frames while each of the respective light sources 112, 114, and 116 is activated. In this embodiment the image sensor 152 would not require a Bayer mask or any other color filter. The pixels of the image sensor 152 would thus be responsive to a wide range of wavelengths produced by the sources 112, 114, and 116. Each frame in sequence is thus associated with a particular illumination wavelength band or color and may be captured at the full spatial resolution of the image sensor. The frame capture rate may be increased to account for the additional time required to capture successive red, green, and blue frames. For example, a conventional frame rate for CCD and CMOS image sensors is about 30 frames per second (fps) and the frame rate may be increased to 90 fps or higher on some available sensors to substantially reduce color/time artifacts associated with the sequential frame capture.

In another embodiment the controller 132 may be alternatively or additionally configured to control the relative energy produced by the light sources 112, 114, and 116. Typical CMOS or CCD image sensors are more responsive to green light wavelengths and less responsive to blue and red wavelengths and the controller 132 may be configured to increase the power level of the light sources that generate red and blue wavelengths or to reduce the power level of the light source that generates the green wavelength, thus compensating for the non-uniform wavelength response of the image sensor. Control of individual power levels of the plurality of sources is useful for optimizing the sensor dynamic range and signal-to-noise characteristics.

Additionally or alternatively, the power level of the respective light sources may also be controlled to produce a desired spectral illumination characteristic for the illuminated region 240. In some cases features of objects within the object field 180 may be enhanced when illuminated by light having a specific spectral characteristic. For example, in laparoscopic surgery, illumination having an increased intensity of the blue spectral content may help to reveal cancerous lesions that are less visible under uniform RGB or white light illumination conditions. Vascular features may also be enhanced by a more intense near infrared (NIR) spectral component. The controller 132 and the use of separate sources 112, 114, and 116 facilitate such a configuration.

Figure 5:
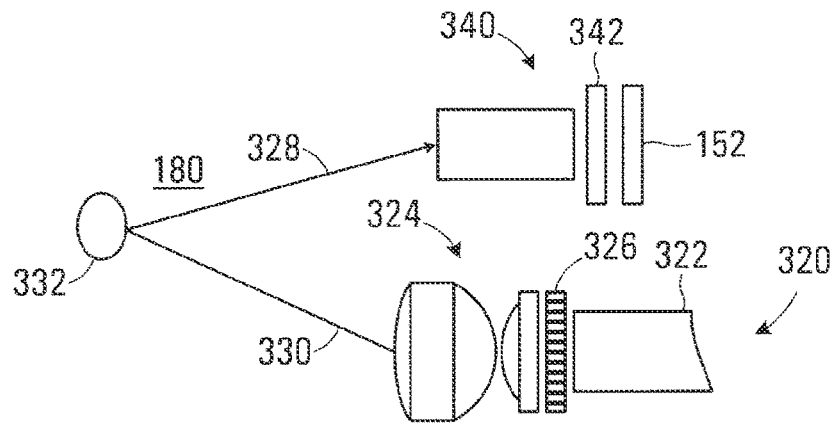
FIG. 5 is a plan view of an alternative embodiment an illuminator apparatus.

An embodiment of an illuminator and camera for reducing the effect of specular reflections is shown in FIG. 5. Referring to FIG. 5, an illuminator apparatus 320 is shown having an integrating element 322 (shown in part) and an illumination projector 324. The illumination projector 324 includes a first polarizer 326 that passes light having a specific linear polarization direction and absorbs or reflects light having other polarization directions. The projected illumination thus has a single linear polarization direction. A specular reflection 328 of an illumination beam 330 from an object 332 within the object field 180 may be captured by a camera 340 and will have a polarization direction that is maintained during the reflection while diffuse reflections from other objects within the object field 180 will give rise to reflections having pseudo-random polarization directions. In this embodiment the camera 340 includes a second polarizer 342 in front of the image sensor 152 that is oriented to absorb or reflect light having the same polarization direction as the specularly reflected illumination beam 330 while passing a useful portion light having various polarization directions caused by diffuse reflections. Specular reflections at the image sensor 152 are thus largely attenuated by the second polarizer 342 reducing their intensity. The embodiment shown in FIG. 5 thus has the effect of reducing glare from smooth or wet surfaces within the object field 180, for example tools or wet tissues within a body cavity of a patient undergoing laparoscopic surgery.

The disclosed embodiments may be implemented to provide an illuminator apparatus for an imaging system that has the illuminated region tailored to correspond to the object field associated with the camera. The illuminated region has a shape, size, and aspect ratio that generally correspond to the shape, size, and aspect ratio to the imaged object field. The illuminator apparatus thus more efficiently illuminates the object field thereby reducing possible temperature increases due to heat generated during operation of the camera 140 and illuminator apparatus 100, which may be problematic in applications such as laparoscopic surgery. Reduced heat generation may also improve reliability and reduce manufacturing costs of the camera 140 and illuminator apparatus 100. Efficient projection of the illumination into the object field 180 enables the sources to be run at a lower power, which permits the system to be reduced in size for ease of use and portability.

While specific embodiments have been described and illustrated, such embodiments should be considered illustrative only and not as limiting the invention as construed in accordance with the accompanying claims.

What is claimed is:

1. An imaging system comprising:
   at least one input light source;
   an integrating element comprising an input end and an output face, the integrating element being configured to receive the at least one input light source at the input end and to produce a generally homogenous illumination beam at the output face;
   an illumination projector being configured to project an image of the output face of the integrating element onto an object field to produce an illuminated region of the object field; and
   an imaging apparatus comprising an image sensor, the image sensor being configured to image a portion of the object field corresponding to the illuminated region of the object field,
   wherein images captured by the image sensor are captured through a polarizer having a polarization direction operable to reduce specular reflections from objects within the object field.

2. The system of claim 1, wherein the image sensor comprises a first aspect ratio, wherein the illuminated region of the object field comprises a second aspect ratio, and wherein the first aspect ratio and the second aspect ratio are substantially equivalent.

3. The system of claim 1, wherein the illuminated region is sized such that the image sensor is configured to be at least partly overfilled in at least one direction.

4. The system of claim 1, wherein the at least one input light source comprises a plurality of light sources, and wherein each of the plurality of light sources is configured to generate a respective input light beam.

5. The system of claim 4, wherein the plurality of light sources comprises at least two of:
   a red light source;
   a green light source;
   a blue light source; or
   a tunable light source.

6. The system of claim 4 further comprising a controller being configured to:
   sequentially activate each of the plurality of light sources to cause the object field to be sequentially illuminated by each of the respective input light beam;
   synchronize the image sensor to capture separate image frames while the object field is being illuminated by each of the respective input light beam; and
   combine the captured separate image frames to produce a combined image of the object field.

7. The system of claim 6, wherein the image sensor comprises a plurality of sensor elements, wherein each of the plurality of sensor elements is responsive to light having spectral properties encompassing spectral properties of each of the respective input light beam, and wherein the separate image frames are captured using all of the plurality of sensor elements.

8. The system of claim 4 further comprising a controller being configured to control respective power levels of each of the plurality of light sources to produce a desired spectral illumination characteristic for the illuminated region.

9. The system of claim 8, wherein the desired spectral illumination characteristic is selected to enhance certain features within the object field.

10. A method for illuminating an object field comprising:
    coupling at least one input light source into an input end of an integrating element, the integrating element being configured to produce a generally homogeneous illumination beam at an output face of the integrating element; and
    projecting an image of the output face of the integrating element onto the object field to produce an illuminated region of the object field,
    wherein images captured by an image sensor are captured through a polarizer having a polarization direction operable to reduce specular reflections from objects within the object field.

11. The method of claim 10 further comprising using the image sensor to image a portion of the object field, wherein the illuminated region of the object field corresponds to the illuminated region of the object field.

12. The method of claim 11, wherein the image sensor comprises a first aspect ratio, wherein projecting the image further comprises producing the illuminated region such that the illuminated region comprises a second aspect ratio, and wherein the first aspect ratio and the second aspect ratio are substantially equivalent.

13. The method of claim 11, wherein projecting the image further comprises sizing the illuminated region such that the image sensor is configured to be at least partly overfilled in at least one direction.

14. The method of claim 11, wherein the at least one input light source comprises a plurality of input light source, and wherein the method further comprises:
    receiving at least one input light beam; and
    activating the plurality of input light sources, each of the plurality of input light sources being operable to produce a respective input light beam.

15. The method of claim 14 further comprising:
    sequentially activating each of the plurality of input light sources to cause the object field to be sequentially illuminated by each of the respective input light beams;
    synchronizing the image sensor to capture separate image frames while the object field is being illuminated by each of the respective input light beams; and
    combining the captured separate image frames to produce a combined image of the object field.

16. The method of claim 15, wherein the image sensor comprises a plurality of sensor elements, wherein each of the plurality of sensor elements is responsive to light having spectral properties encompassing each of the respective input light beams, and wherein the separate image frames are captured using all of the plurality of sensor elements.

* * * * *